(12) United States Patent
Wang (10) Patent No.: US 11,574,740 B2
(45) Date of Patent: Feb. 7, 2023

(54) ELECTRONIC DEVICE AND METHOD FOR SUPPRESSING VISION LOSS

(71) Applicants: CLEAR ELECTRON CO., Ltd., Tokyo (JP); WITWOT Inc., Syracuse, NY (US)

(72) Inventor: Yi Wang, Beijing (CN)

(73) Assignees: CLEAR ELECTRON CO., LTD., Tokyo (JP); WITWOT INC., Syracuse, NY (US)

( * ) Notice: Subject to any disclaimer, the term of this patent is extended or adjusted under 35 U.S.C. 154(b) by 0 days.

(21) Appl. No.: 17/471,677

(22) Filed: Sep. 10, 2021

(65) Prior Publication Data
US 2022/0130551 A1     Apr. 28, 2022

(30) Foreign Application Priority Data
Oct. 27, 2020  (JP) .............................. JP2020-179808

(51) Int. Cl.
*G16H 50/30* (2018.01)
*G16H 40/63* (2018.01)
*G02C 11/00* (2006.01)
*G08B 21/18* (2006.01)

(52) U.S. Cl.
CPC ............. *G16H 50/30* (2018.01); *G02C 11/10* (2013.01); *G08B 21/18* (2013.01); *G16H 40/63* (2018.01); *G02C 2202/06* (2013.01)

(58) Field of Classification Search
CPC ........ G16H 50/30; G16H 40/63; G16H 50/20; G02C 11/10; G02C 2202/06; G08B 21/18; G06K 9/6276; G06K 9/6288
See application file for complete search history.

(56) References Cited

U.S. PATENT DOCUMENTS

| | | | | |
|---|---|---|---|---|
| 2015/0332576 A1* | 11/2015 | Son | ........................ | G09G 5/003 351/158 |
| 2016/0274381 A1* | 9/2016 | Haddadi | ................. | G08B 21/18 |
| 2020/0409182 A1* | 12/2020 | Endoh | .................... | G02C 7/104 |

FOREIGN PATENT DOCUMENTS

| | | | | | |
|---|---|---|---|---|---|
| CN | 111243742 A | * | 6/2020 | ............. | G02C 11/10 |
| CN | 111243742 A | | 6/2020 | | |
| JP | S62157007 A | | 7/1987 | | |
| JP | 2004045831 A | | 2/2004 | | |
| JP | 2007212501 A | | 8/2007 | | |
| JP | 2016538588 A | | 12/2016 | | |

* cited by examiner

*Primary Examiner* — Brian Wilson
(74) *Attorney, Agent, or Firm* — Jordan IP Law, LLC (57) ABSTRACT

An electronic device comprises a distance detecting sensor for detecting a distance from a user to a target object, a light detecting sensor for detecting light intensity of external environment, a nine-axis sensor for detecting the user's motion, a control unit for determining whether the user is at high risk of vision loss based on the distance information output from the distance detecting sensor, the light intensity information output from the light detecting sensor, and the motion information output from the nine-axis sensor, and generating an alert command when it is determined that the user is at high risk of vision loss; and a vibrator for providing an alert based on the alert command output from a control unit.

12 Claims, 7 Drawing Sheets

ELECTRONIC DEVICE AND METHOD FOR SUPPRESSING VISION LOSS

CROSS-REFERENCE TO RELATED APPLICATION

The present application claims priority under 35 U.S.C. § 119 to Japanese Patent Application No. 2020-179808 (filed 27 Oct. 2020), which is hereby incorporated by reference in its entirety.

TECHNICAL FIELD

The present invention relates to an electronic device and a method for suppressing vision loss.

BACKGROUND ART

CN207037259U discloses vision loss suppressing eyeglasses comprising a distance detecting sensor for detecting a distance from a user to a disc; a processor for determining whether the distance from the user to the disc is appropriate based on distance information, and for generating an alert command when the distance is determined to be inappropriate; and a speaker for providing an alert based on the alert command.

SUMMARY OF INVENTION

However, in the vision loss suppressing eyeglasses described in Patent Document 1, only distance information is used to generate alert commands, and thus the reliability of the alert commands generated in this way is low. In some cases, it may not be possible to effectively suppress the vision loss of the user.

The present invention has been made to solve the problem described above, and an object thereof is to provide an electronic device and a method for suppressing vision loss that can effectively suppress the user's vision loss.

According to one aspect of the present invention, there is provided an electronic device comprising: a distance detecting portion for detecting a distance from a user to a target object; a light detecting portion for detecting light intensity of external environment; a motion detecting portion for detecting the user's motion; a controller for determining whether the user is at high risk of vision loss based on the distance information output from the distance detecting portion, the light intensity information output from the light detecting portion, and the motion information output from the motion detecting portion, and generating an alert command when it is determined that the user is at high risk of vision loss; and an alerting portion for providing an alert based on the alert command output from a controller.

According to another aspect of the present invention, there is provided a method for suppressing vision loss including: an information acquisition step for acquiring distance information from a user to a target object, light intensity information of an external environment, and user's motion information; a risk determination step for determining whether the user is at high risk of vision loss based on the distance information, light intensity information, and motion information acquired in the information acquisition step; and an alert command generating step to generate an alert command when the risk determination step determines that the risk of vision loss for the user is high.

According to these aspects, it is possible to effectively suppress the user's vision loss.

DESCRIPTION OF EMBODIMENTS

An embodiment of the present invention will be described with reference to the drawings. The same configuration elements are denoted by the same reference numerals in this description.

(Configuration of the Vision Loss Suppressing Eyeglasses)

The configuration of vision loss suppressing eyeglasses 1 according to the present embodiment will be described with reference to FIG. 1 to FIG. 6.

Figure 1:
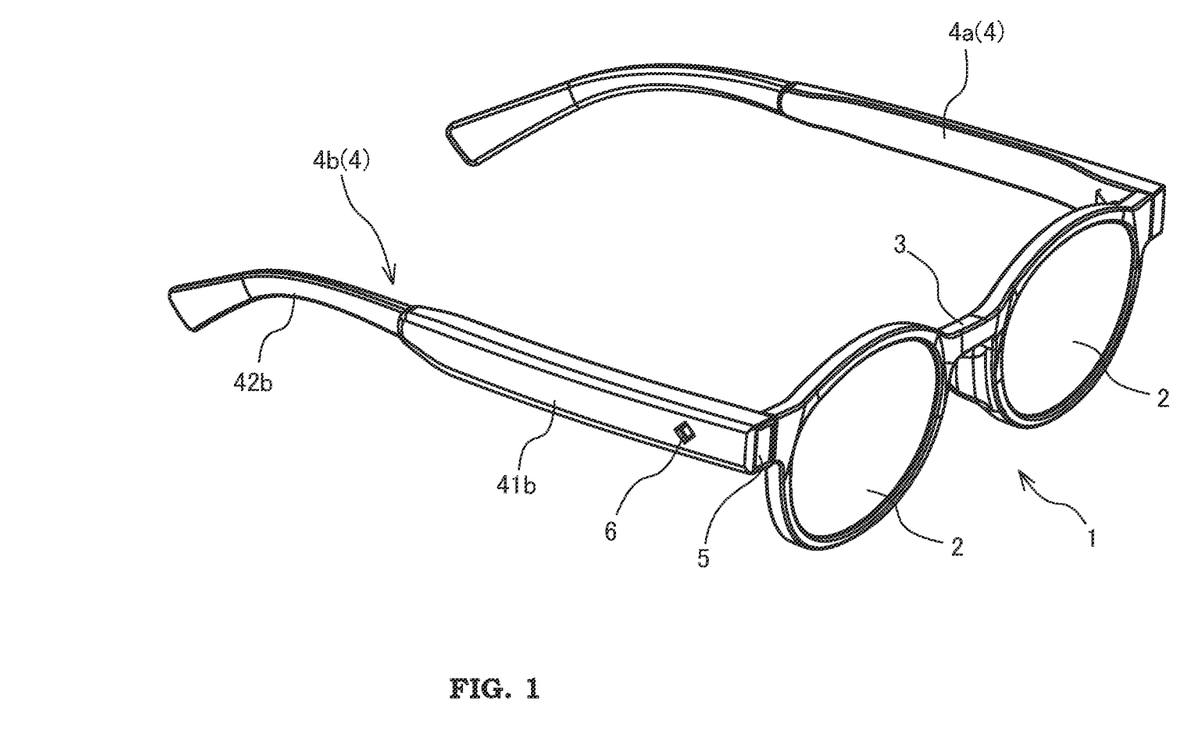
FIG. 1 is an oblique perspective view of vision loss suppressing eyeglasses.
Figure 2:
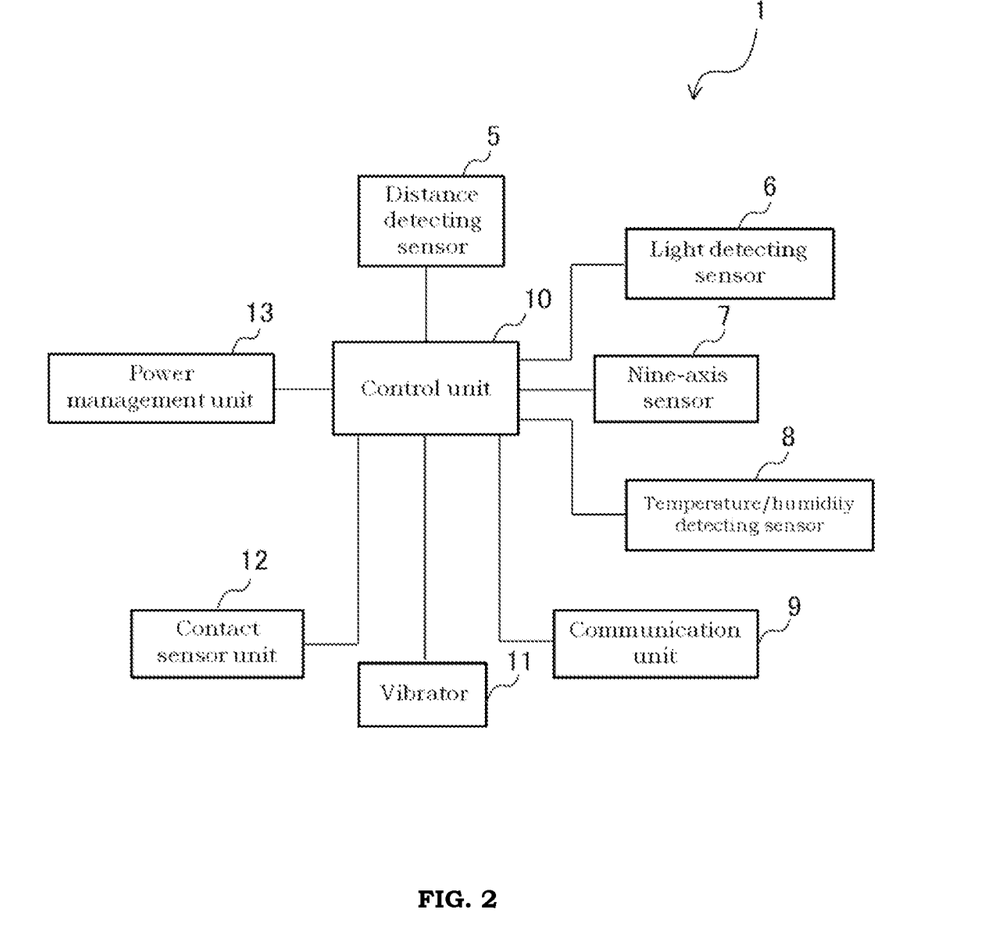
FIG. 2 is a schematic block diagram of vision loss suppressing eyeglasses.
Figure 3:
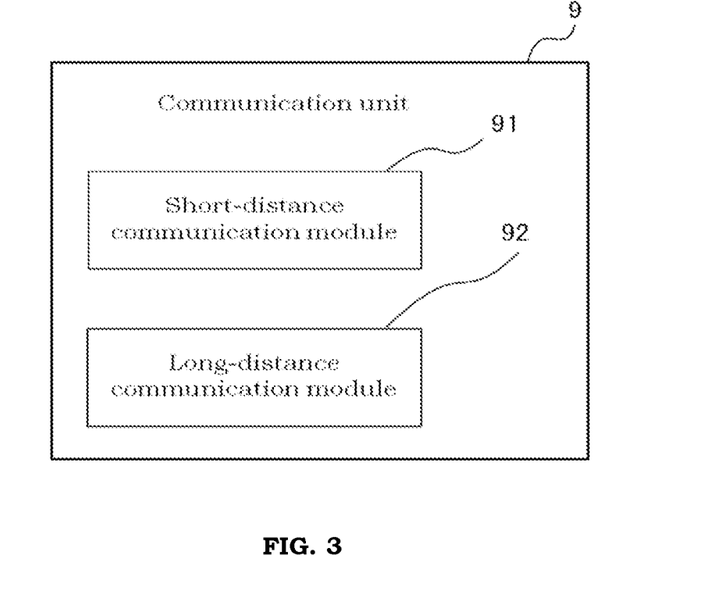
FIG. 3 is a schematic block diagram of a communication unit.
Figure 4:
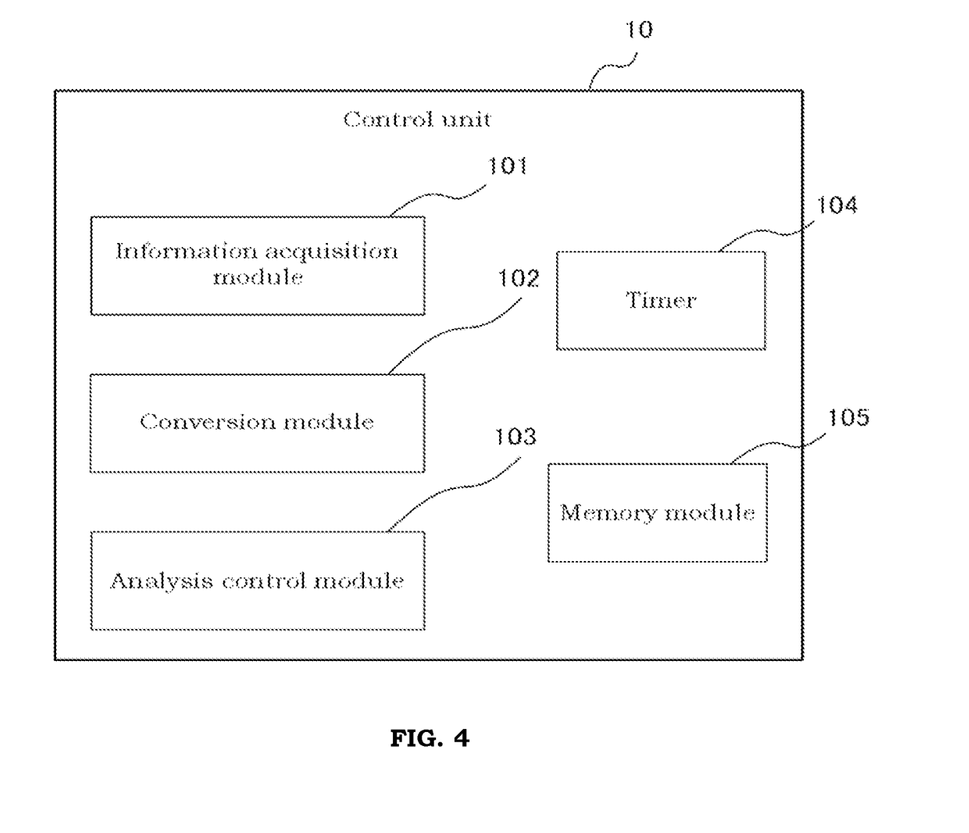
FIG. 4 is a schematic block diagram of a control unit.
Figure 5:
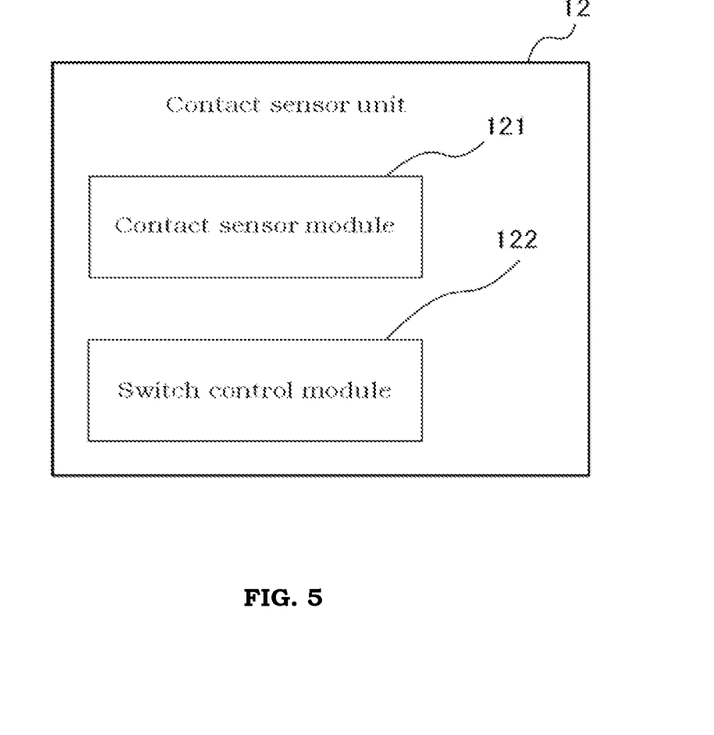
FIG. 5 is a schematic block diagram of a contact sensor unit.
Figure 6:
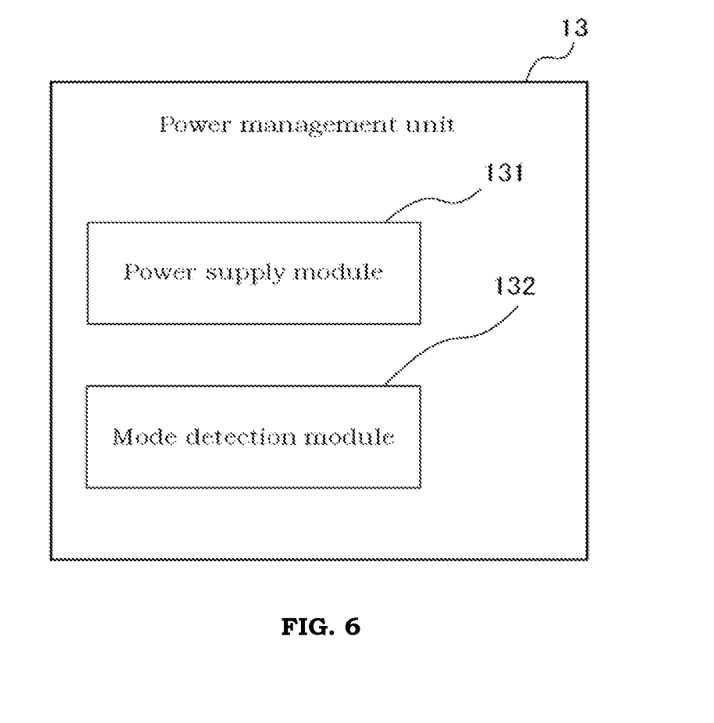
FIG. 6 is a schematic block diagram of a power management unit.

FIG. 1 is an oblique perspective view showing the vision loss suppressing eyeglasses 1 according to the embodiment of the present invention. FIG. 2 is a schematic block diagram showing the vision loss suppressing eyeglasses 1. FIG. 3 is a schematic block diagram of a communication unit 9. FIG. 4 is a schematic block diagram of a control unit 10. FIG. 5 is a block diagram of a contact sensor unit 12. FIG. 6 is a block diagram of a power management unit 13.

As shown in FIG. 1 and FIG. 2, the vision loss suppressing eyeglasses 1 according to the present embodiment is an electronic device (specifically, smart eyeglasses) for suppressing vision loss of the user. The vision loss suppressing eyeglasses 1 comprises, in addition to lenses 2, a lens holding frame 3, and two leg portions 4, a distance detecting sensor 5 as its distance detecting portion, a light detecting sensor 6 as its light detecting portion, a nine-axis sensor 7 as its motion detecting portion, a temperature/humidity detecting sensor 8 as its temperature/humidity detecting portion, a communication unit 9 as its communication portion, a control unit 10 as its controller, a vibrator 11 as its alerting portion, a contact sensor unit 12 as its contact sensor, and a power management unit 13.

The lenses 2 are used to correct the user's vision. The lenses 2 may be constituted of glass material or resin material, as needed. The lenses 2 which do not correct the vision of the user are applicable.

The lens holding frame 3 is a frame for holding the lenses 2. In the present embodiment, the lens holding frame 3 is made of resin material, but is not limited thereto, and may be made of metal material such as titanium alloy.

The two leg portions 4 are hinged to both sides of the lens holding frame 3 via hinge connections (not shown in figures). The two leg portions 4 are made of, for example, resin material. The two leg portions 4 are constituted of a left leg portion 4a and a right leg portion 4b. The left leg portion 4a and the right leg portion 4b have the same external shape.

The left leg portion 4a is molded by resin material such that the leg portion 4a is solid. On the other hand, the right leg portion 4b has a hollow housing portion 41b and a solid ear-hanging part 42b connected to the rear end of the housing portion 41b as one of its ends.

A distance detecting sensor 5, a light detecting sensor 6, a nine-axis sensor 7, a temperature/humidity detecting sensor 8, a communication unit 9, a control unit 10, a vibrator 11, a contact sensor unit 12, and a power management unit 13 are contained in the housing portion 41b. Further, the distance detecting sensor 5, light detecting sensor 6, nine-axis sensor 7, temperature/humidity detecting sensor 8, communication unit 9, vibrator 11, contact sensor unit 12, and power management unit 13 are electrically connected to the control unit 10 via electrical wiring.

Thus, since the distance detecting sensor 5, the light detecting sensor 6, the nine-axis sensor 7, the temperature/humidity detecting sensor 8, the communication unit 9, the control unit 10, the vibrator 11, the contact sensor unit 12 and the power management unit 13 are integrated into the housing portion 41b of the right leg portion 4b, compared with the vision loss suppressing eyeglasses where the distance detecting sensor 5, the light detecting sensor 6, the nine-axis sensor 7, temperature/humidity detecting sensor 8, communication unit 9, control unit 10, vibrator 11, contact sensor unit 12, and power management unit 13 are distributed over various parts (specifically, the lens holding frame 3 and the two leg portions 4) of the vision loss suppressing eyeglasses 1, electrical wiring becomes easier and manufacturing costs can be substantially reduced. In addition, if any of the parts is broken, it will be sufficient to replace only the broken part, which also reduces the cost of use for the user.

The distance detecting sensor 5 is a sensor for detecting the distance (i.e., viewing distance) from the user (specifically, the vision loss suppressing eyeglasses 1) to a target object (for example, a viewing object such as a book, TV, smartphone or tablet device). In the present embodiment, the distance detecting sensor 5 is constituted of a laser distance detecting sensor that converts the time from the transmission of a laser beam to the reception of the laser beam into a distance, but is not limited thereto. It may be constituted of, for example, an ultrasonic distance detecting sensor. The distance detected by the distance detecting sensor 5 is used to determine whether the user is at high risk of vision loss.

The light detecting sensor 6 is a sensor for detecting the light intensity of the external environment. In the present embodiment, the light detecting sensor 6 is constituted of photoresistors. The light intensity detected by the light detecting sensor 6 is used to determine whether the user is at high risk of vision loss.

The nine-axis sensor 7 is a gyro-sensor for detecting the (three-dimensional) motion of the user. Specifically, the nine-axis sensor 7 detects the rotation angle of the user's head (hereinafter referred to simply as the rotation angle) in three dimensions. More specifically, the nine-axis sensor 7 detects the rotation angle in the tilt direction and the rotation angle in the pan direction of the user's head. The user's rotation angle detected by the nine-axis sensor 7 is used to determine whether the user is at high risk of vision loss.

In the present embodiment, the nine-axis sensor 7 consists of sensors that detect angles, but is not limited thereto; for example, it may consist of a gyro sensor that detects angular velocity or angular acceleration. In this case, the control unit 10 calculates the rotation angle in the tilt direction and the rotation angle in the pan direction of the user's head based on the angular velocity and angular acceleration output from the nine-axis sensor 7.

The temperature/humidity detecting sensor 8 is a sensor for detecting the temperature and humidity of the external environment. Specifically, the temperature/humidity detecting sensor 8 consists of a temperature detecting sensor for detecting the temperature of the external environment and a humidity detecting sensor for detecting the humidity of the external environment. The temperature and humidity of the external environment detected by the temperature/humidity detecting sensor 8 are used to determine whether the user is indoors or outdoors.

The communication unit 9 is, for example, a unit capable of communicating with a communication terminal (not shown in figures) such as a smart phone or tablet. The communication unit 9 enables the vision loss suppressing eyeglasses 1 to send data to and receive data from the communication terminal. As shown in FIG. 3, in the present embodiment, the communication unit 9 is constituted of a short-distance communication module 91, such as Bluetooth (registered trademark), which can communicate with a communication terminal over a short distance, and a long-distance communication module 92, such as WIFI (registered trademark), which can communicate with a communication terminal over a long distance. However, it is not limited thereto. For example, it may be configured with either the short-distance communication module 91 or the long-distance communication module 92 only.

The communication unit 9 is a unit that receives various communication information from a communication terminal, including update information for updating a plurality of posture modes or predetermined threshold conditions to be described later, and weather information that includes outdoor temperature and humidity information. The update information received by the communication unit 9 is used to update the posture modes or the predetermined threshold conditions. The predetermined threshold conditions are used to determine whether the user is at high risk of vision loss. On the other hand, the weather information received by the communication unit 9 is used to determine whether the user is indoors or not.

The control unit 10 is a controller that controls each process of the vision loss suppressing eyeglasses 1. In the present embodiment, the control unit 10 is constituted of a CPU as a computer, but it is not limited thereto; for example, it may be constituted of a plurality of microcomputers.

In the present embodiment, the control unit 10 determines whether the user is at high risk of vision loss based on the viewing distance output from the distance detecting sensor 5, the light intensity output from the light detecting sensor 6, and the rotation angle output from the nine-axis sensor 7. When it is determined that the user is at high risk of vision loss, the control unit 10 generates an alert command. This allows us to determine whether the user is at high risk of vision loss based on the viewing distance as well as the light intensity and rotation angle. As a result, the reliability of the alert command can be improved compared to the conventional vision loss suppressing eyeglasses that determine whether the user is at high risk of vision loss based only on the distance information and generate an alert command based on the result of the determination that the user is at high risk of vision loss. As a result, the user's vision loss can be effectively suppressed.

Specifically, as shown in FIG. 4, the control unit 10 has an information acquisition module 101, a conversion module 102, an analysis control module 103, a timer 104 as a time detecting portion, and a memory module 105. Each module of the control unit 10 may be configured either by hardware or by software.

The information acquisition module 101 is one for obtaining various parameter information (specifically, distance information from the user to the target object (i.e., viewing distance information, hereinafter referred to simply as "distance information") output from each sensor (specifically, the distance detecting sensor 5, the light detecting sensor 6, the nine-axis sensor 7, and the temperature/humidity detecting sensor 8, etc.), light intensity information, and user's movement information), and various communication information from the communication terminal output from communication unit 9.

The conversion module 102 is a module for converting the various parameter information acquired by the information acquisition module 101 into converted parameter information that can be read by the analysis control module 103. For example, the conversion module 102 converts the various parameter information acquired by the information acquisition module 101 from analog format to digital format.

The analysis control module 103 is a module for analyzing the various converted parameter information converted by the conversion module 102 and constructing a user's behavioral model. Specifically, the analysis control module 103 generates data samples as training samples by analyzing the various converted parameter information, and uses the generated data samples to construct a behavioral model containing a plurality of behavioral modes (i.e., posture modes) of the user based on an algorithm of machine learning (specifically, a neural network). Using the generated data samples, a model of the user's behavior including multiple modes (i.e., posture modes) is constructed based on a machine learning (specifically, neural network) algorithm. In this way, the multiple posture modes and behavioral models can be obtained with high accuracy. The multiple posture modes of the user are used to identify the postures of the user, and include, for example, learning/reading posture modes, TV viewing posture modes, and device viewing posture modes.

The neural network constructed by the analysis control module 103 is a three-layer neural network. The three-layer neural network includes a first hidden layer that learns edge features, a second hidden layer that learns shape features consisting of edges, and a third hidden layer that learns pattern features consisting of shapes.

The analysis control module 103 is also a module for executing each process of the vision loss suppressing eyeglasses 1. Each process executed by the analysis control module 103 will be described later.

The timer 104 is a timer for detecting the time period over which the user maintains the same posture (in this case, the learning/reading posture). The posture of the user includes, for example, learning/reading posture, TV viewing posture, and device viewing posture. In the present embodiment, the timer 104 is built into the control unit 10, but it is not limited thereto; for example, it may be provided separately from the control unit 10. The time detected by the timer 104 is used to determine whether the posture holding time of the user holding a certain posture is too long beyond the allowable time corresponding to that posture.

The memory module 105 is a memory for storing various converted parameter information converted by the conversion module 102, predetermined threshold conditions, predetermined postures, and allowable times. The memory module 105 also stores a processing program or an algorithm program to be executed in the analysis control module 103. In the present embodiment, the memory module 105 is built into the control unit 10, but it is not limited thereto; for example, it may be provided separately from the control unit 10.

Furthermore, the memory module 105 stores the data samples generated by the analysis control module 103 and the user's behavioral model constructed by the analysis control module 103. The data sample includes parameters such as the user's postures, viewing distance (distance from the vision loss suppressing eyeglasses 1 to the viewed object), viewing time, and light intensity. The data sample is a combinatorial vector consisting of grayscale features, HOG features, LBP features and Haar-Like features of patterns.

The vibrator 11 provides an attention-arousing alert by vibrating based on the alert commands, etc. output from the control unit 10. The user receives different alerts, realizes that there is a high risk of vision loss or that the posture holding time for holding the same posture is too long, and corrects the posture or improves the environment (brighten the room) or takes a break. In the present embodiment, the alerting portion is constituted of a vibrator 11, but it is not limited thereto; for example, it may be constituted of a speaker or buzzer that sounds based on an alert command, etc. Or, it may be constituted of a combination of a vibrator 11 and a speaker. In this case, it is possible to identify that there is a high risk of vision loss and that the posture holding time is too long.

The contact sensor unit 12 is a unit for switching on the power supply module 131 described below, which functions as the power supply of the vision loss suppressing eyeglasses 1, from off state upon contact with the user. As shown in FIG. 5, the contact sensor unit 12 is constituted of a contact sensor module 121 that senses contact with the user, a switch control module 122 that switches on the power supply module 131 of the vision loss suppressing eyeglasses 1 from off state when the contact with the user is sensed by the contact sensor module 121. The switch control module 122 switches off the power supply module 131 of the vision loss suppressing eyeglasses 1 from on state when the contact with the user is no longer sensed by the contact sensor module 121.

In this way, by configuring the contact sensor unit 12 from the contact sensor module 121 and the switch control module 122, not only the switching of the power supply of the vision loss suppressing eyeglasses 1 can be easily achieved, but the operation of switching on or off the power supply of the vision loss suppressing eyeglasses 1 becomes no longer necessary as well. As a result, malfunctions can be avoided in the switching of the power supply of the vision loss suppressing eyeglasses 1. In addition, since the switching of the power supply of the vision loss suppressing eyeglasses 1 is performed only by the contact sensor unit 12 without the control of the control unit 10, the switching of the power supply of the vision loss suppressing eyeglasses 1 can be made faster and simpler.

The power management unit 13 is a unit for battery charge management, normal operation management or low-power operation management. As shown in FIG. 6, the power management unit 13 is constituted of a power supply module 131 that supplies power to the vision loss suppressing eyeglasses 1, and a mode detection module 132 that detects the use mode of the vision loss suppressing eyeglasses 1. The control unit 10 selects from the battery charge management, normal operation management or low-power operation management based on the use mode of the vision loss suppressing eyeglasses 1 detected by the mode detection module 132.

(Operating Process of the Vision Loss Suppressing Eyeglasses)

The operating process of the vision loss suppressing eyeglasses 1 is described below with reference to FIG. 7.

Figure 7:
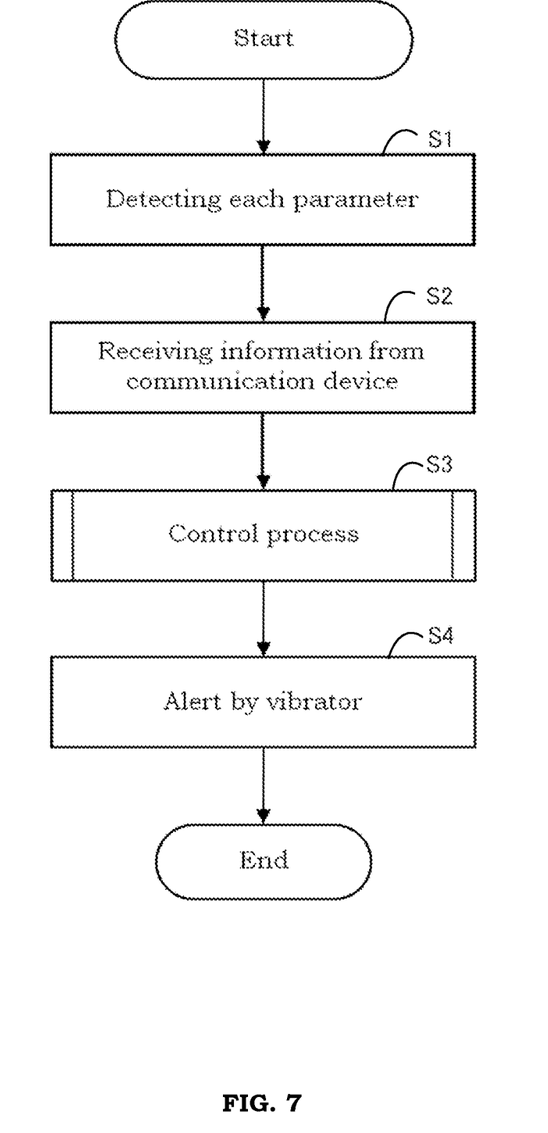
FIG. 7 is a flowchart showing an operating process of the vision loss suppressing eyeglasses.

FIG. 7 is a flowchart showing the operating process of the vision loss suppressing eyeglasses 1.

When the vision loss suppressing eyeglasses 1 are wore on the user's head, the contact sensor module 121 of the contact sensor unit 12 detects contact between the vision loss suppressing eyeglasses 1 and the user, and the switch control module 122 of the contact sensor unit 12 switches the power supply module 131 of the vision loss suppressing eyeglasses 1 from off to on. The power supply module 131 then switches from off to on. The power supply module 131 then supplies power to each electronic component of the vision loss suppressing eyeglasses 1.

As a result, the operating process of the vision loss suppressing eyeglasses 1 is started and proceeds to step S1.

As shown in FIG. 7, first, in step S1, each sensor (specifically, the distance detecting sensor 5, the light detecting sensor 6, the nine-axis sensor 7, and the temperature/humidity detecting sensor 8) detects each parameter (specifically, the distance from the user to the target object, light intensity, motion, and temperature/humidity) every predetermined time (for example, one minute). Then, each sensor outputs each parameter information detected during the predetermined time to the control unit 10 and proceeds to step S2.

Next, in step S2, the communication unit 9 receives various types of information, including at least the weather information, from the communication terminal. Then, the communication unit 9 outputs the various information received to the control unit 10, and proceeds to step S3.

Next, in step S3 as a control process, the control unit 10 performs a control process based on each parameter output from each sensor and various information output from the communication unit 9 to generate an alert command. Then, the control unit 10 outputs the generated alert command to the vibrator 11. The details of the control process by the control unit 10 will be described later.

Next, in step S4, the vibrator 11 vibrates based on the alert command output from the control unit 10 to provide an attention-arousing alert. As a result, the user realizes that there is a high risk of vision loss or that the posture holding time for holding the same posture is too long, and can correct the posture or improve the environment (brighten the room) or take a break as appropriate.

Finally, when the vision loss suppressing eyeglasses 1 are removed from the user's head, the contact sensor module 121 no longer detects contact between the vision loss suppressing eyeglasses 1 and the user, and the switch control module 122 switches the power supply module 131 from on to off. The power supply module 131 will then stop supplying power to the electronic components of the vision loss suppressing eyeglasses 1. As a result, the operating process of the vision loss suppressing eyeglasses 1 is ended.

In the present embodiment, step S2 is performed after step S1, but it is not limited thereto. For example, it may be performed before step S1, or it may be performed simultaneously with step S1.

Figure 8:
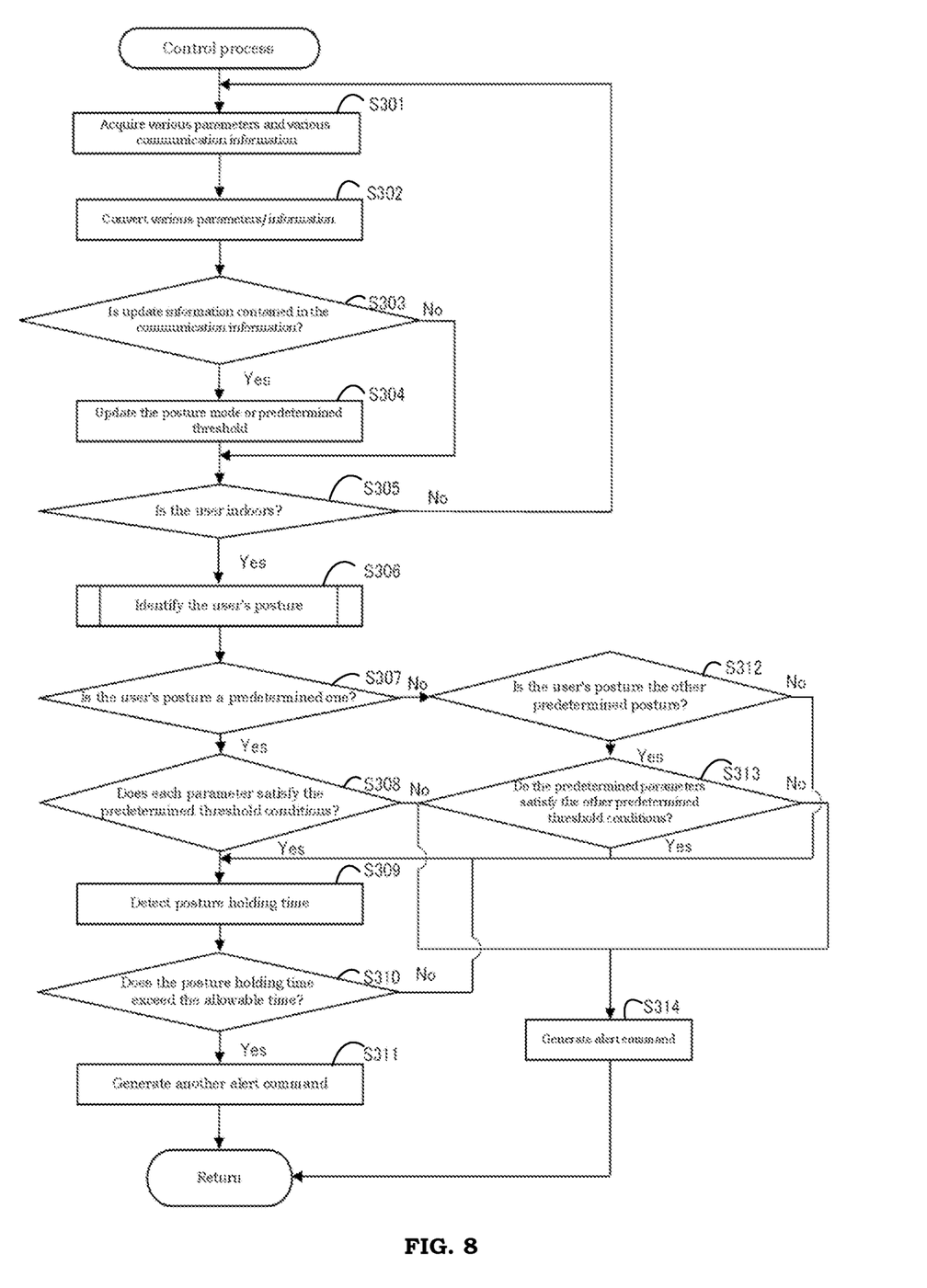
FIG. 8 is a flowchart showing a control process in the operating process of the vision loss suppressing eyeglasses.

The following explains the control process S3 by the control unit 10 with reference to FIG. 8.

FIG. 8 is a flowchart showing the control process S3 in the operating process of the vision loss suppressing eyeglasses 1.

As shown in FIG. 8, first, in step S301 as the information acquisition step, the information acquisition module 101 of the control unit 10 obtains various parameter information (specifically, the distance information, light intensity information, rotation angle information, and temperature and humidity information) output from each sensor (specifically, the distance detecting sensor 5, the light detecting sensor 6, the nine-axis sensor 7, and the temperature/humidity detecting sensor 8) during each predetermined time (for example, one minute), and various communication information from the communication terminal output from the communication unit 9. Then, the information acquisition module 101 outputs the various parameter information and various communication information acquired to the conversion module 102 and the analysis control module 103 respectively, and proceeds to step S32.

Next, in step S302, the conversion module 102 converts the various parameter information output from the information acquisition module 101 from analog format to digital format. Then, the conversion module 102 outputs the various converted parameter information to the analysis control module 103 and proceeds to step S3.

Next, in step S303, the analysis control module 103 determines whether the various communication information output from the information acquisition module 101 includes update information for updating the multiple posture modes or the predetermined threshold conditions. When the various communication information contains update information for updating the multiple posture modes or the predetermined threshold conditions (in the case of Yes), it proceeds to step 304. On the other hand, if the various communication information does not contain the update information for updating the multiple posture modes or the predetermined threshold conditions (in the case of No), it proceeds to step S305 without going through step S304. That is, in step S303, when the analysis control module 103 determines that the various communication information does not contain update information for updating the multiple posture modes or the predetermined threshold conditions, it proceeds to step S305 without updating the posture modes or the predetermined threshold conditions.

Next, if it is Yes in step S303, in step S304, the analysis control module 103 updates the multiple posture modes or predetermined threshold conditions in the behavioral model of the user stored in the memory module 105 to the multiple posture modes or predetermined threshold conditions based on the update information, and proceeds to step S305. This allows the setting and updating of posture modes or predetermined threshold conditions to be easily performed by the communication terminal. This eliminates the need for a separate setting change portion in the vision loss suppressing eyeglasses 1 to update the posture modes or predetermined threshold conditions, and simplifies the configuration of the vision loss suppressing eyeglasses 1.

Next, in the case of No in step S303 or of proceeding from step S304, in step S305, the analysis control module 103 outputs the temperature and humidity information output from the conversion module 102, and the outdoor temperature and humidity information of the weather information contained in the various communication information, which is output from the information acquisition module 101. This makes it possible to accurately determine whether the user is indoors or not. In addition, the control unit 10 does not identify the posture of the user when it determines that the user is not indoors, but identifies the posture of the user only when it determines that the user is indoors, thereby further improving the reliability of the alert command. As a result, the user's vision loss can be suppressed more effectively.

Then, if the user is indoors (in the case of Yes), the system proceeds to step S306, which is an identification process of the user's posture, and if the user is not indoors (in the case of No), the system returns to step S301. In other words, when the analysis control module 103 determines that the user is outdoors in step S305, no alert command is generated and the vibrator 11 does not vibrate.

Next, if it is Yes in step S305, in step S306, the analysis control module 103 identifies the posture of the user based on the converted distance information, the converted light intensity information, and the converted motion information (specifically, the converted rotation angle information) output from the conversion module 102 in such a way that it can be assigned (classified) to any one of the multiple posture modes of the user in the behavioral model of the user stored in the memory module 105, and proceeds to step S307. The details of step S306 (identification of the user's posture) will be described later.

Next, in step S307, the analysis control module 103 determines whether the identified posture of the user is a predetermined posture (in this case, a learning/reading posture) stored in the memory module 105.

Then, if the identified posture of the user is the learning/reading posture (in the case of Yes), i.e., if it is necessary to determine whether the user is at high risk of vision loss, it proceeds to step S308. On the other hand, if the identified posture of the user is not the learning/reading posture (in the case of No), it proceeds to step S312. That is, if, in step S307, the analysis control module 103 determines that the identified posture of the user is not the learning/reading posture (that is, it is the TV viewing posture or the device viewing posture), it proceeds to step S312. This can further improve the reliability of the alert command, and thus more effectively suppress the user's vision loss.

Next, in step S308 as a risk determination step in the case of Yes in step S307, the analysis control module 103 determines whether the distance based on the converted distance information corresponding to the identified posture of the user, the light intensity based on the converted light intensity information, and the rotation angle based on the converted rotation angle information all satisfy their corresponding predetermined threshold conditions (specifically, the predetermined distance threshold condition, the predetermined light intensity threshold condition, and the predetermined angle threshold condition). In other words, in step S308, the analysis control module 103 determines whether the user is at high risk of vision loss based on the distance information, light intensity information, and rotation angle information.

Here, the predetermined distance threshold condition means that the distance from the user to the target object is 30 cm or more, the predetermined light intensity threshold condition means that the light intensity is 300 Lux or more, and the predetermined angle threshold condition means that the rotation angle is 15° or less. These predetermined threshold conditions can be changed via the communication terminal.

Then, if the distance, light intensity and rotation angle satisfy the predetermined distance threshold condition, predetermined light intensity threshold condition and predetermined angle threshold condition respectively (in the case of Yes), proceed to step S309. In this case, in step S308, the analysis control module 103 determines that the user is not at risk of vision loss. On the other hand, if the distance, light intensity, and rotation angle do not satisfy the predetermined distance threshold condition, the predetermined light intensity threshold condition, and the predetermined angle threshold condition respectively (in the case of No), that is, if at least one of the distance, light intensity, and rotation angle does not satisfy at least one of the predetermined distance threshold condition, the predetermined light intensity threshold condition, and the predetermined angle threshold condition, proceed to step S314. In this case, in step S308, the analysis control module 103 determines that the user is at high risk of vision loss.

Next, in step S314 as the step for generating the alert command when it is No in step S308, the analysis control module 103 generates an alert command for posture correction or environment improvement (brighten the room) in response to the user's high risk of vision loss. Then, the analysis control module 103 outputs the generated alert command to the vibrator 11, ends the control process, and returns to the operating process shown in FIG. 7.

On the other hand, in the case of Yes in step S308, and No in step S312 described below, or Yes in step S313, then in step S309, the timer 104 detects the posture holding time in which the user holds the same posture. Then, the timer 104 outputs the detected posture holding time to the analysis control module 103 and proceeds to step S310.

Next, in step S310, the analysis control module 103 determines whether the posture holding time output from the timer 104 exceeds the allowable time (for example, 30 minutes) stored in the memory module 105.

If the posture holding time exceeds the allowable time (in the case of Yes), the system proceeds to step S311, and if the posture holding time does not exceed the allowable time (in the case of No), the system returns to step S309. As a result, even when there is no need to determine whether the user has a high risk of vision loss or not, or even when the user has a low risk of vision loss, a rest-promoting alert command can be generated, so that the user can be effectively restrained from viewing for a long time.

Next, in step S311, when it is Yes in step S310, the analysis control module 103 generates an alert command for promoting rest as another alert command different from the alert command for correcting posture or improving the environment, given that the posture holding time for holding the same posture is too long. Then, the analysis control module 103 outputs the generated alert command for promoting rest to the vibrator 11, ends the control process S3, and returns to the operating process shown in FIG. 7.

On the other hand, if it is No in step S307, in step S312, the analysis control module 103 determines whether the identified posture of the user is another predetermined posture (in this case, a device viewing posture) stored in the memory module 105.

Then, when the identified posture of the user is the device viewing posture (in the case of Yes), that is, when it is necessary to determine whether the user is at high risk of vision loss, it proceeds to step S313. On the other hand, if the identified posture of the user is not the device viewing posture (in the case of No), proceed to step S309. In other words, if the analysis control module 103 determines in step S312 that the identified posture of the user is not the device viewing posture (i.e., it is the TV viewing posture), it proceeds to step S309. This can further improve the reliability of the alert command, and thus more effectively suppress the user's vision loss.

Next, in step S313 as a risk determination step in the case of Yes in step S312, the analysis control module 103 determines whether the distance based on the converted distance information as a predetermined parameter corresponding to the identified posture of the user satisfies the other predetermined threshold condition corresponding thereto (specifically, the other predetermined distance threshold condition only) are satisfied or not. In other words, in step S313, the analysis control module 103 determines, based on the distance information, whether the user is at high risk of vision loss.

Here, the other predetermined threshold condition (the other predetermined distance threshold condition) means that the distance from the user to the target object is 30 cm or more. The other predetermined threshold condition can be changed via the communication terminal.

In the present embodiment, the other predetermined threshold conditions consist only of the other predetermined distance threshold condition, but it is not limited thereto; for example, it may consist of both the other predetermined distance threshold condition and the other predetermined angle threshold condition.

Then, if the distance satisfies the other predetermined distance threshold condition (in the case of Yes), proceed to step S309. In this case, in step S313, the analysis control module 103 determines that the user is not at risk of vision loss. On the other hand, if the distance does not satisfy the other predetermined distance threshold condition (in the case of No), proceed to step S314. In this case, in step S308, the analysis control module 103 determines that the user is at high risk of vision loss.

Next, in step S314 as the step for generating alert command when it is No in step S313, the analysis control module 103 generates an alert command for posture correction in response to the user's high risk of vision loss. Then, the analysis control module 103 outputs the generated alert command to the vibrator 11, ends the control process, and returns to the operating process shown in FIG. 7.

Figure 9:
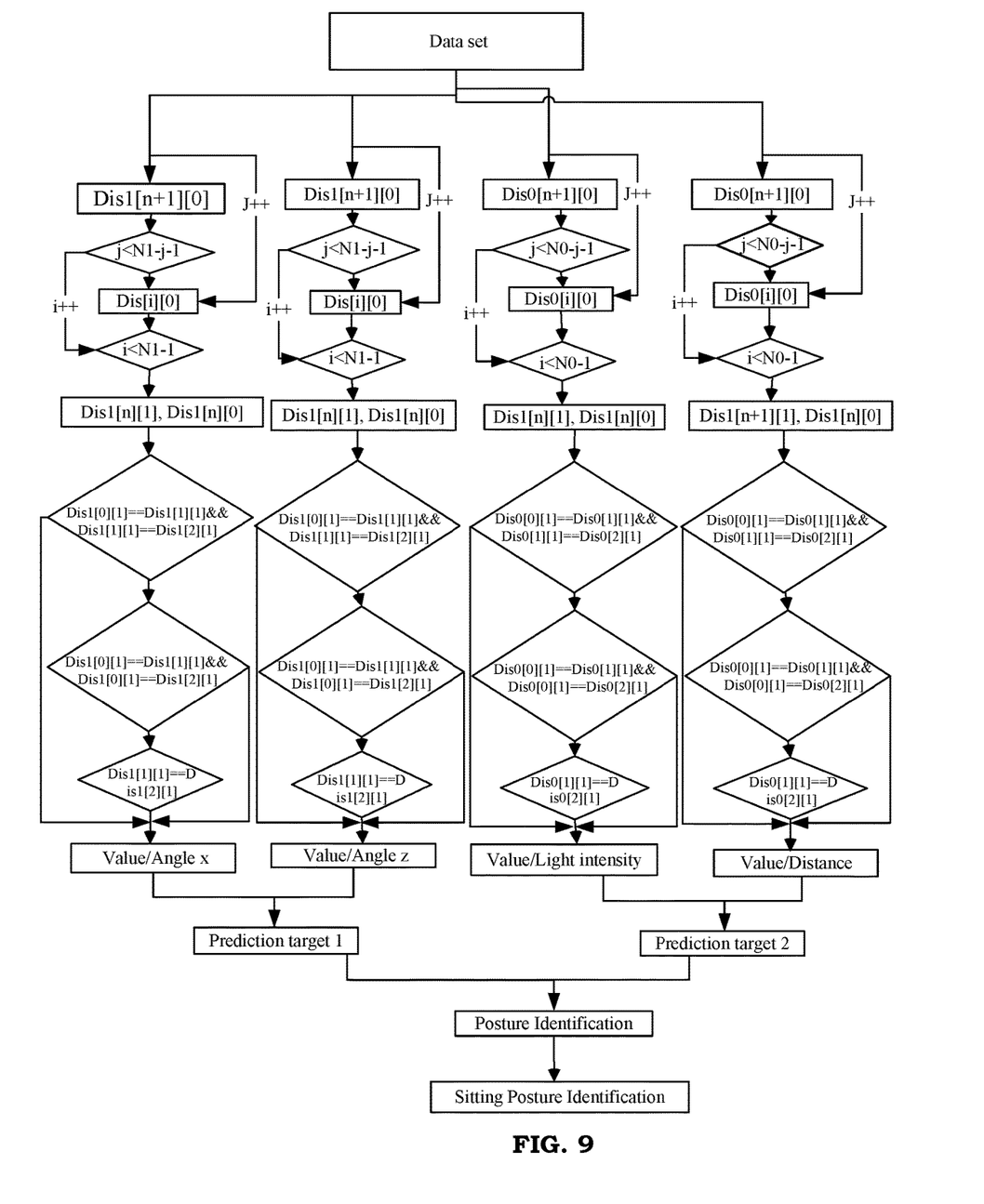
FIG. 9 is a flowchart showing a process of identifying the user's posture in the control process.

The following describes the identification process S306 of the user's posture in the control process S3 with reference to FIG. 9.

FIG. 9 is a KNN flowchart showing the identification process S306 of the user's posture in the control process S3.

As shown in FIG. 9, first, the analysis control module 103 normalizes the data samples based on the converted distance information, converted light intensity information, and converted rotation angle information output from the conversion module 102.

Next, the analysis control module 103 sets a parameter (for example, k).

Next, the analysis control module 103 stores the most adjacent historical data (tilt-direction rotation angle, pan-direction rotation angle, light intensity, and viewing distance) by maintaining a priority level array of size k, where the distances are arranged in order from the largest to the smallest. Then, the analysis control module 103 randomly selects k sets of data from the historical data as the first most adjacent tuples. Each set contains two elements DataSet[n][0] and DataSet[n][1], where DataSet[n][0] and DataSet[n][1] correspond to the distance and standard classification result of the k sensor data respectively. The analysis control module 103 then stores the k sets of history codes and distances in the priority level array.

Next, by traversing the training tuple set, the analysis control module 103 calculates the distance between each output parameter information (tilt-direction rotation angle z, pan-direction rotation angle x, light intensity, viewing distance) and the k tuples of historical data. The distance is displayed using Dis[n][0], and the classification result is displayed using Dis[n][1]. Then, the analysis control module 103 compares the calculated distance L with the maximum distance Lmax of the priority level array. If the distance L is greater than or equal to Lmax, the analysis control module 103 abandons that tuple. On the other hand, when the distance L is smaller than Lmax, the analysis control module 103 deletes the maximum distance tuple of the priority level array and stores the current training tuple in the priority level array.

Next, the analysis control module 103 calculates the majority category of the k tuples in the priority level array as the classification result value of the test tuple.

Next, after calculating the classification result values for each of the parameters (tilt-direction rotation angle z, pan-direction rotation angle x, light intensity, and viewing distance), the analysis control module 103 identifies the posture of the user in such a way that the posture of the user is assigned (classified) to any one of the multiple posture modes of the user in the behavioral model of the user, and ends the identification process S306 of the posture of the user and returns to the control process S3 shown in FIG. 8.

(Effect)

Next, the effect of the present embodiment will be explained.

The vision loss suppressing eyeglasses 1 of the present embodiment comprises a distance detecting sensor 5 for detecting the distance from the user to the target object, a light detecting sensor 6 for detecting the light intensity of the external environment, a nine-axis sensor 7 for detecting the user's motion, a control unit 10 for determining whether the user is at high risk of vision loss, based on the distance information output from the distance detecting sensor 5, the light intensity information output from the light detecting sensor 6, and the motion information output from the nine-axis sensor 7, and generating an alert command when it is determined that the user is at high risk of vision loss, and a vibrator 11 for providing the alert based on the alert command output from the control unit 10.

The method for suppressing vision loss according to the present embodiment comprises an information acquisition step S301 for acquiring the distance information from the user to a target object, the light intensity information of an external environment, and the motion information of the user, and a risk determination step S308 for determining whether a risk of vision loss of the user is high or not based on the distance information, light intensity information, and motion information acquired in the information acquisition step S301, and an alert command generating step S314 for generating an alert command when it is determined that the user is at high risk of vision loss in the risk determination step S308.

According to these configurations, it is possible to determine whether the user is at high risk of vision loss based on the light intensity information and the rotation angle information in addition to the distance information. Compared to conventional vision loss suppressing eyeglasses, which determine whether the user is at high risk of vision loss based only on distance information and generate an alert command based on the result of the determination that the user is at high risk of vision loss, the reliability of the alert command can be improved. As a result, the user's vision loss can be effectively suppressed.

In the present embodiment, the control unit 10 identifies the posture of the user based on the distance information, the light intensity information, and the rotation angle information in such a way that it can be assigned to any one of a plurality of predetermined posture modes, determines whether the identified posture of the user is a predetermined posture, and, when it is determined that the identified posture of the user is a predetermined posture, determines whether the distance, light intensity, and rotation angle corresponding to the identified posture of the user satisfy the predetermined threshold conditions, and, when it is determined that the distance, light intensity, or rotation angle do not satisfy the predetermined threshold conditions, generates an alert command.

According to this configuration, the control unit 10 identifies the posture of the user based on the distance information, the light intensity information, and the rotation angle information, determines whether the identified posture of the user is a predetermined posture, and, when the identified posture of the user is a predetermined posture, that is, when it is necessary to determine whether the user is at high risk of vision loss, determines whether the distance, light intensity, and rotation angle corresponding to the identified posture of the user satisfy the predetermined threshold conditions. Therefore, in cases where it is not necessary to determine whether the user is at high risk of vision loss, no determination will be performed as to whether the distance, light intensity and rotation angle corresponding to the identified posture of the user satisfy the predetermined threshold conditions, and the reliability of the alert command can be further improved. As a result, the user's vision loss can be suppressed more effectively.

In addition, in the present embodiment, the vision loss suppressing eyeglasses 1 further comprises a timer 104 for detecting the posture holding time in which the user holds the same posture, and the control unit 10 determines whether the identified posture is another predetermined posture when it determines that the identified posture of the user is not one predetermined posture. In the case where it is determined that the identified posture is not another predetermined posture, it determines whether the posture holding time detected by the timer 104 exceeds a predetermined allowable time, and when it is determined that the posture holding time exceeds the allowable time, it generates another alert command that is different from the alert command.

According to this configuration, when it is determined that the identified posture of the user is not one predetermined posture, the control unit 10 determines whether the identified posture is another predetermined posture, and when the identified posture is not another predetermined posture, that is, when it is not necessary to determine whether the user is at high risk of vision loss, it determines whether the posture holding time detected by the timer 104 exceeds the predetermined allowable time. When it is determined that the posture holding time exceeds the allowable time, it generates another alert command that is different from the alert command, therefore, it is possible to generate an alert command for promoting rest even when it is not necessary to determine whether the user is at high risk of vision loss. As a result, it is possible to effectively inhibit users from viewing for a long time.

In addition, in the present embodiment, when the control unit 10 determines that the identified posture is another predetermined posture, it determines whether the distance (a predetermined parameter) satisfies the other predetermined distance threshold condition (another predetermined threshold condition). When it determines that the predetermined parameter does not satisfy the other predetermined threshold conditions, it generates an alert command.

According to this configuration, when it is determined that the distance information (a predetermined parameter) does not satisfy the other predetermined distance threshold condition (the other predetermined threshold condition), i.e., when it is determined that the risk of the user's vision loss is high, an alert command can be generated, hence further improving the reliability of the alert command. As a result, the user's vision loss can be more effectively suppressed.

In the present embodiment, when the control unit 10 determines that the distance (a predetermined parameter) satisfies the other predetermined distance threshold condition (the other predetermined threshold condition), the control unit 10 determines whether the posture holding time detected by the timer 104 exceeds a predetermined allowable time, and, when it is determined that the posture holding time exceeds the allowable time, it generates another alert command that is different from the alert command.

According to this configuration, when the control unit 10 determines that the distance information (the predetermined parameter) satisfies other predetermined distance threshold conditions (the other predetermined threshold conditions), that is, when it determines that the risk of vision loss of the user is low, the control unit 10 determines whether the posture holding time detected by the timer 104 exceeds a predetermined allowable time, and if it is determined that the posture holding time exceeds the allowable time, it generates another alert command that is different from the alert command. Therefore, the system can generate alert commands for promoting rest even when the user's risk of vision loss is low. As a result, it is possible to effectively inhibit the user from viewing for a long time.

In addition, in the present embodiment, the vision loss suppressing eyeglasses 1 further comprises a timer 104 for detecting the posture holding time in which the user holds the same posture, and the control unit 10 determines whether the posture holding time detected by the timer 104 exceeds a predetermined allowable time when it is determined that the distance information, light intensity information, or motion information satisfies the predetermined threshold conditions. When it is determined that the posture holding time exceeds the allowable time, it generates another alert command that is different from the alert command.

According to this configuration, when the control unit 10 determines that the distance information, light intensity information, or motion information satisfies the predetermined threshold conditions, that is, when it determines that the risk of vision loss of the user is low, the control unit 10 determines whether the posture holding time detected by the timer 104 exceeds a predetermined allowable time, and if it is determined that the posture holding time exceeds the allowable time, it generates another alert command that is different from the alert command. Therefore, the system can generate alert commands for promoting rest even when the user's risk of vision loss is low. As a result, it is possible to effectively inhibit the user from viewing for a long time.

Moreover, in the present embodiment, the user's behavioral model, which contains a plurality of posture modes, is constructed based on a machine learning algorithm.

According to this configuration, since the behavioral model of the user containing a plurality of posture modes is constructed based on a machine learning algorithm, the multiple posture modes and the behavioral model can be obtained with high accuracy.

In the present embodiment, the user's posture is identified based on a machine learning algorithm.

According to this configuration, since the user's posture is identified based on a machine learning algorithm, the user's posture can be identified with high accuracy.

In the present embodiment, the vision loss suppressing eyeglasses 1 further comprises a communication unit 9 that receives update information for updating the multiple posture modes or predetermined threshold conditions from a communication terminal, and the control unit 10 updates the multiple posture modes or predetermined threshold conditions based on the update information output from the communication unit 9.

According to this configuration, since the control unit 10 updates the multiple posture modes or predetermined threshold conditions based on the update information from the communication unit 9, the setting and updating of the posture modes or predetermined threshold conditions can be easily performed by the communication terminal. This eliminates the need for a separate setting change portion in the vision loss suppressing eyeglasses 1 to update the posture modes or predetermined threshold conditions, and simplifies the configuration of the vision loss suppressing eyeglasses 1.

In the present embodiment, the vision loss suppressing eyeglasses 1 further comprises a temperature/humidity detecting sensor 8 for detecting the temperature and humidity of the external environment, the communication unit 9 receives weather information including outdoor temperature and humidity information from a communication terminal, and the control unit 10 determines whether the user is indoors or not based on the temperature and humidity information output from the temperature/humidity detecting sensor 8 and the outdoor temperature and humidity information of the weather information output from the communication unit 9, and identifies the posture of the user when it is determined that the user is indoors.

According to this configuration, since the control unit 10 determines whether the user is indoors based on the temperature and humidity information output from the temperature/humidity detecting sensor 8 and the outdoor temperature and humidity information of the weather information output from the communication unit 9, it can accurately determine whether the user is indoors or not. In addition, since the control unit 10 does not identify the posture of the user when it determines that the user is not indoors, and identifies the posture of the user only when it determines that the user is indoors, the reliability of the alert command can be further improved. As a result, the user's vision loss can be suppressed more effectively.

The present embodiment further comprises a contact sensor unit 12 for switching the power supply from off to on upon contact with the user. The contact sensor unit 12 has a contact sensor module 121 for sensing contact with the user, and a switch control module 122 for switching the power supply from off to on when the contact with the user is sensed by the contact sensor module 121.

According to this configuration, by configuring the contact sensor unit 12 from the contact sensor module 121 and the switch control module 122, not only the switching of the power supply of the vision loss suppressing eyeglasses 1 can be easily achieved, but the operation of switching on or off the power supply of the vision loss suppressing eyeglasses 1 becomes no longer necessary as well. As a result, malfunctions can be avoided in the switching of the power supply of the vision loss suppressing eyeglasses 1. In addition, since the switching of the power supply of the vision loss suppressing eyeglasses 1 is performed only by the contact sensor unit 12 without the control of the control unit 10, the switching of the power supply of the vision loss suppressing eyeglasses 1 can be made faster and simpler.

Modification Examples

In the above-mentioned embodiment, the vision loss suppressing eyeglasses 1 comprises a distance detecting sensor 5, a light detecting sensor 6, a nine-axis sensor 7, and a temperature/humidity detecting sensor 8 as sensors to detect each parameter, but it is not limited thereto; for example, it may dispense with the temperature/humidity detecting sensor 8, and comprise only the dispense with the distance detecting sensor 5, the light detecting sensor 6, and the nine-axis sensor 7. In this case, it is not necessary for the communication unit 9 to receive weather information including outdoor temperature and humidity information. Furthermore, the control process S3 will not include step S305 to determine whether the user is indoors or not.

In the above-described embodiment, the posture of the user is identified based on a machine learning algorithm, but this is not limited thereto; for example, the posture may be identified based on predetermined distance tolerance range, light intensity tolerance range, and rotation angle tolerance range corresponding to each posture mode.

In the above-described embodiment, the allowable time is set in advance to be unchangeable and stored in the memory module 105, but this is not limited thereto; for example, it may be changeable depending on the communication terminal. In this case, the allowable time change information for changing the allowable time is received by the communication unit 9 from the communication terminal.

Although the present embodiments and modifications have been described above, the above-mentioned embodiments and modifications are merely examples of the application of the present invention, and the technical scope of the present invention is not intended to be limited to the specific configurations of the above-mentioned embodiments.

This application claims priority based on Japanese Patent Application No. 2020-179808 filed with the Japan Patent Office on 27 Oct. 2020, the entire contents of this application are incorporated herein by reference.

The invention claimed is:

1. An electronic device, comprising:
    a distance detecting portion for detecting distance information from a user to a target object;
    a light detecting portion for detecting light intensity information of an external environment;
    a motion detecting portion for detecting a user's motion information;
    a controller for determining whether the user is at high risk of vision loss based on the distance information, the light intensity information, and the user's motion information, and generating a first alert command when it is determined that the user is at high risk of vision loss, wherein
    the controller identifies a posture of the user based on the distance information, the light intensity information, and the user's motion information in such a way that the identified posture is assignable to any one of a plurality of predetermined posture modes, and determines whether the identified posture of the user is a predetermined posture,
    when it is determined that the identified posture of the user is the predetermined posture, the controller determines whether the distance information, the light intensity information, and the user's motion information corresponding to the identified posture of the user satisfy predetermined threshold conditions, and
    when it is determined that one or more of the distance information, the light intensity information, or the user's motion information does not satisfy the predetermined threshold conditions, the controller generates the first alert command; and an alerting portion for providing an alert based on the first alert command output from the controller.

2. The electronic device according to claim 1, which further comprises:
a time detecting portion for detecting a posture holding time in which the user holds the same posture.

3. The electronic device according to claim 2, wherein
when it is determined that the identified posture of the user is not the predetermined posture, the controller determines whether the identified posture is another predetermined posture,
when it is determined that the identified posture is not the another predetermined posture, the controller determines whether the posture holding time exceeds a predetermined allowable time, and
when it is determined that the posture holding time exceeds the predetermined allowable time, the controller generates a second alert command that is different from the first alert command.

4. The electronic device according to claim 3, wherein
when it is determined that the identified posture is the another predetermined posture, the controller determines whether a predetermined parameter satisfies other predetermined threshold conditions, and
when it is determined that the predetermined parameter does not satisfy the other predetermined threshold conditions, the controller generates the first alert command.

5. The electronic device according to claim 4, wherein
when it is determined that the predetermined parameter satisfies the other predetermined threshold conditions, the controller determines whether the posture holding time exceeds the predetermined allowable time, and
when it is determined that the posture holding time exceeds the predetermined allowable time, the controller generates a second alert command that is different from the first alert command.

6. The electronic device according to claim 2, wherein
when it is determined that the distance information, the light intensity information, or the user's motion information satisfies the predetermined threshold conditions, the controller determines whether the posture holding time exceeds a predetermined allowable time, and
when it is determined that the posture holding time exceeds the predetermined allowable time, the controller generates a second alert command that is different from the first alert command.

7. The electronic device according to claim 1, wherein
a user's behavioral model that contains the plurality of the predetermined posture modes is constructed based on a machine learning algorithm.

8. The electronic device according to claim 1, wherein the posture of the user is identified based on a machine learning algorithm.

9. The electronic device according to claim 1, which further comprises:
a communication portion for receiving update information for updating the plurality of the predetermined posture modes or the predetermined threshold conditions from a communication terminal;
wherein the controller updates the plurality of the predetermined posture modes or the predetermined threshold conditions based on the update information output from the communication portion.

10. The electronic device according to claim 9, which further comprises:
a temperature/humidity detecting portion for detecting temperature and humidity of the external environment;
wherein the communication portion receives weather information including outdoor temperature and humidity information of the external environment from the communication terminal; and
the controller determines whether the user is indoors or not based on the temperature and the humidity of the external environment and the outdoor temperature and humidity information, and identifies a posture of the user when it is determined that the user is indoors.

11. The electronic device according to claim 1, which further comprises:
a contact sensor portion for switching a power supply from off to on by contacting with the user;
wherein the contact sensor portion comprises:
a contact sensor portion module for sensing contact with the user, and
a switch control module for switching the power supply from off to on when the contact with the user is sensed by the contact sensor module.

12. A method for suppressing vision loss, comprising:
an information acquisition step for acquiring distance information from a user to a target object, light intensity information of an external environment, and user's motion information;
a risk determination step for determining whether the user is at high risk of vision loss based on the distance information, the light intensity information, and the user's motion information, wherein the risk determination step comprises:
an identifying step for identifying a posture of the user based on the distance information, the light intensity information, and the user's motion information in such a way that the identified posture is assignable to any one of a plurality of predetermined posture modes, and determines whether the identified posture of the user is a predetermined posture, and
a determining step for determining, when it is determined that the identified posture of the user is the predetermined posture, whether the distance information, the light intensity information, and the user's motion information corresponding to the identified posture of the user satisfy predetermined threshold conditions; and
an alert command generating step for generating an alert command when it is determined that the user is at high risk of vision loss in the risk determination step, wherein the alert command generating step generates the alert command when it is determined that one or more of the distance information, the light intensity information, or the user's motion information does not satisfy the predetermined threshold conditions.

* * * * *